United States Patent [19]

Yachigo et al.

[11] 4,385,143
[45] May 24, 1983

[54] STABILIZER FOR SYNTHETIC RESINS

[75] Inventors: Shinichi Yachigo, Toyonaka; Yuko Takahashi, Minoo; Tsutomu Mitsuda, Kishiwada; Mitsuhisa Nakatani, Osaka, all of Japan

[73] Assignee: Sumitomo Chemical Company, Limited, Osaka, Japan

[21] Appl. No.: 298,111

[22] Filed: Aug. 31, 1981

[30] Foreign Application Priority Data

Sep. 26, 1980 [JP] Japan ................. 55-134818
Sep. 30, 1980 [JP] Japan ................. 55-137229
Jan. 6, 1981 [JP] Japan ................. 56-959
Jan. 23, 1981 [JP] Japan ................. 56-9316
Jan. 26, 1981 [JP] Japan ................. 56-10541
Jan. 27, 1981 [JP] Japan ................. 56-11869

[51] Int. Cl.³ .............. C07C 69/612; C07D 251/34; C08K 5/13; C08K 5/24
[52] U.S. Cl. .................. 524/101; 524/291; 524/302; 524/304; 524/305; 544/221; 560/75
[58] Field of Search .............. 524/101, 291, 302; 544/221; 560/75

[56] References Cited

U.S. PATENT DOCUMENTS 3,285,855 11/1966 Dexter et al. .............. 252/57
3,629,194 12/1971 Onishi et al. .............. 524/302
3,763,093 10/1973 Kletecka et al. .............. 524/101
3,862,053 1/1975 Susi .............. 524/101
3,988,363 10/1976 Spivack et al. .............. 560/75
4,032,562 6/1977 Dexter et al. .............. 560/75

OTHER PUBLICATIONS

Nishinaga et al., Synthesis, pp. 553-554, 1976.

Primary Examiner—John Kight, III
Assistant Examiner—R. A. White
Attorney, Agent, or Firm—Stevens, Davis, Miller & Mosher

[57] ABSTRACT

Synthetic resins, particularly polyolefins, are markedly improved in their resistances to heat and oxidation by the incorporation of a 2-methyl-4-t-butyl-5-hydroxyphenylalkanoic acid ester alone or in combination with a thioether-type antioxidant represented by the general formula

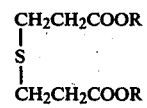

wherein R represents an alkyl group of 12 to 20 carbon atoms, or by the general formula

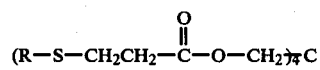

wherein R represents an alkyl group of 4 to 20 carbon atoms.

35 Claims, No Drawings

STABILIZER FOR SYNTHETIC RESINS

This invention relates to novel stabilizers for synthetic resins. More particularly, it relates to esters of 2-methyl-4-t-butyl-5-hydroxyphenylalkanoic acids and to a stabilized synthetic resin composition comprising the said compound incorporated therein.

Because of their excellent physical, chemical, and electrical properties, synthetic resins are used in diversified fields after having been processed into molded articles, pipes, sheets and films by various methods such as blow molding, extrusion molding, injection molding, calendering, and the like. It is well known, however, that if used in an unstabilized form, synthetic resins are degraded by the action of heat and oxygen during processing or in service, thus bringing about marked deterioration in their physical properties accompanied with a phenomenon of softening, becoming brittle, or discoloration.

In order to prevent the occurrence of such phenomena, various antioxidants of the phenol type, phosphorus- or sulfur-containing type have heretofore been added to the synthetic resins during their manufacture or processing.

The present inventors carried out extensive studies to develop excellent antioxidants for use in synthetic resins and, as a result, found that an excellent effect on the resistances of synthetic resins against heat and oxygen is exhibited when the resins are incorporated with a 2-methyl-4-t-butyl-5-hydroxyphenylalkanoic acid ester, which is a novel unprecedented compound represented by the general formula (I)

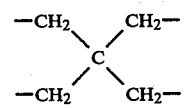  (I)

wherein A represents an alkylene group of 1 to 4 carbon atoms and n is an integer of 1, 3, or 4; when n=1, R represents an alkyl group of 1 to 20 carbon atoms; when n=3, R represents a group of the formula

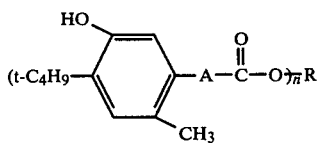

and the novel compound is represented by the general formula (II)

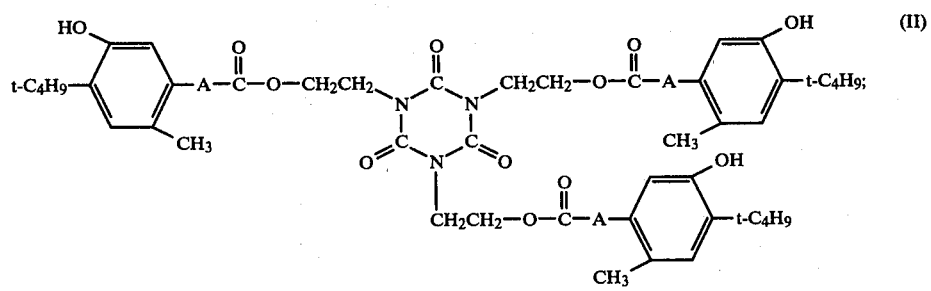  (II)

when n=4, R represents a group of the formula

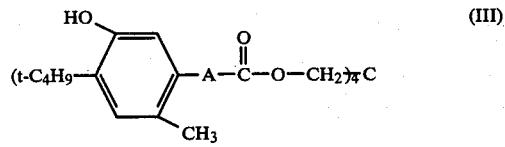

and the novel compound is represented by the general formula (III)

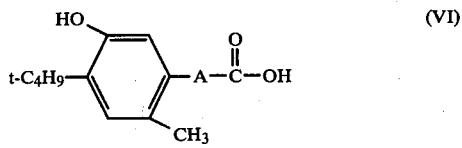  (III)

This invention has been accomplished based on the above findings.

An object of this invention is to provide a novel stabilizer for synthetic resins.

Another object of this invention is to provide a synthetic resin composition stabilized by the incorporation of the said stabilizer.

A further object of this invention is to provide a method for producing the above novel stabilizer.

Other objects and advantages of this invention will become apparent from the following description.

The esters of 2-methyl-4-t-butyl-5-hydroxyphenylalkanoic acids represented by the general formula (I) according to this invention are prepared by reacting, in a known manner, an aliphatic alcohol of 1 to 20 carbon atoms, or 1,3,5-tris(2-tris(2-hydroxyethyl)-s-triazine-2,4,6(1H,3H,5H)-trione, or pentaerythritol with a 2-methyl-4-t-butyl-5-hydroxyphenylalkanoic acid represented by the general formula (VI)

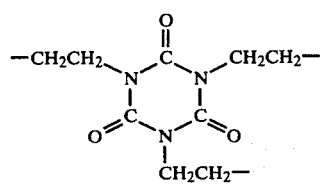  (VI)

or an acid chloride thereof. Further, when n is 1 in the general formula (I), a higher alkyl ester can be obtained by subjecting a lower alkyl ester to an ester interchange with a higher alcohol.

In the general formula (I) of the compounds used in this invention, A represents an alkylene group of 1 to 4 carbon atoms. In view of the performance of the antioxidant, however, an alkylene group of 1 to 3 carbon atoms is preferred. When n is 1, R represents an alkyl group of 1 to 20 carbon atoms. In view of the compatibility with a synthetic resin, volatility, and antioxidant performance, however, an alkyl group of 8 to 20 carbon atoms, particularly octadecyl group, is preferred.

Typical examples of compounds of the general formula (I) used in this invention are as shown in Table 1.

TABLE 1

| No. | Structural formula |
|---|---|
| I-1 | (structure) Octadecyl 2-methyl-4-t-butyl-5-hydroxyphenylacetate |
| I-2 | (structure) Octadecyl 3-(2-methyl-4-t-butyl-5-hydroxyphenyl)propionate |
| I-3 | (structure) Octadecyl 2-(methyl-4-t-butyl-5-hydroxyphenyl)propionate |
| I-4 | (structure) Octyl 2-methyl-4-t-butyl-5-hydroxyphenylacetate |
| I-5 | (structure) t-Butyl 2-methyl-4-t-butyl-5-hydroxyphenylacetate |
| I-6 | (structure) Dodecyl 2-methyl-4-t-butyl-5-hydroxyphenylacetate |
| I-7 | (structure) 1,3,5-tris[2-{2-(4-t-butyl-5-hydroxy-2-methylphenyl)acetyloxy}ethyl]isocyanurate |

TABLE 1-continued

| No. | Structural formula |
|---|---|
| I-8 | (structure) 1,3,5-tris[2-{3-(4-t-butyl-5-hydroxy-2-methylphenyl)propionyloxy}ethyl]isocyanurate |
| I-9 | (structure) 1,3,5-tris[2-{2-(4-t-butyl-5-hydroxy-2-methylphenyl)propionyloxy}ethyl]isocyanurate |
| I-10 | (structure) Tetrakis[2-(4-t-butyl-5-hydroxy-2-methylphenyl)acetyloxymethyl]methane |
| I-11 | (structure) Tetrakis[3-(4-t-butyl-5-hydroxy-2-methylphenyl)propionyloxymethyl]methane |
| I-12 | (structure) Tetrakis[2-(4-t-butyl-5-hydroxy-2-methylphenyl)propionyloxymethyl]methane |

In using the present compound of general formula (I) as an antioxidant for synthetic resins, the amount to be added is generally 0.001 to 5, preferably 0.01 to 2 parts by weight per 100 parts by weight of the resin.

By using the compound of general formula (I) in combination with a known antioxidant of the thioether type represented by the general formula (IV)

wherein R represents an alkyl group of 12 to 20 carbon atoms, it is possible to impart to a synthetic resin synergetically enhanced stabilities against heat and oxygen.

For the said purpose, the total amount to be added of the compound of general formula (I) and the compound of general formula (IV) is 0.001 to 5, preferably 0.01 to 2 parts by weight per 100 parts by weight of the resin. The relative amount of the compound (IV) to the compound (I) is 1 to 10, preferably 2 to 6 parts by weight per part by weight of the compound (I). The alkyl group represented by R in the formula (IV) may have 12 to 20 carbon atoms. In view of commercial availability and economical advantage, a dodecyl, tetradecyl, or octadecyl group is preferred. Examples of such compounds of formula (IV) include dilauryl 3,3'-thiodipropionate, ditetradecyl 3,3'-thiodipropionate, and distearyl 3,3'-thiodipropionate.

Further, an unexpectable and surprising synergetic effect is obtained by using the compound of formula (I) jointly, in a specific ratio, with a known antioxidant of the thioether type represented by the general formula (V)

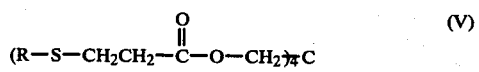

wherein R represents an alkyl group of 4 to 20 carbon atoms. The total amount to be added of the compound of formula (I) and the compound of formula (V) is generally 0.001 to 5, preferably 0.01 to 2 parts by weight for 100 parts by weight of the resin. The weight ratio of the compound of formula (V) to the compound of formula (I) is generally 1 to 10, preferably 2 to 6 per part of the compound of formula (I). R in the formula (V) has 4 to 20 carbon atoms and particularly preferred are hexyl, dodecyl and octadecyl groups. Examples of such compounds are pentaerythritol tetrakis($\beta$-hexylthiopropionate), pentaerythritol tetrakis($\beta$-dodecyl-thiopropionate), and pentaerythritol tetrakis($\beta$-octadecyl thiopropionate).

The compounding of a synthetic resin with the compound of formula (I) according to this invention may be carried out by use of substantially the same known equipment and procedure as used generally in incorporating stabilizers, pigments, fillers and the like into synthetic resins.

The synthetic resin composition of this invention may contain other additives such as, for example, ultraviolet absorbers, light stabilizers, antioxidants, metal inactivators, metallic soaps, neucleating agents, lubricants, antistatics, flame retardants, pigments, and fillers.

The light stability of the present composition can be improved by incorporating an ultraviolet absorber, light stabilizers of the hindered amine type, or the like. Examples of such light stabilizers include 2-hydroxy-4-methoxybenzophenone, 2-hydroxy-4-n-octoxybenzophenone, 2(2'-hydroxy-5'-methylphenyl)benzotriazole, 2(2'-hydroxy-3'-t-butyl-5'-methylphenyl)-5-chlorobenzotriazole, 2(2'-hydroxy-3',5'-di-t-butylphenyl)-5-chlorobenzotriazole, 2(2'-hydroxy-3',5'-diamylphenyl)benzotriazole, [2,2'-thiobis(4-t-octylphenolato)]butylamine nickel salt, 2,2,6,6-tetramethyl-4-piperidinyl benzoate, bis(2,2,6,6-tetramethyl-4-piperidinyl) sebacate, bis(1,2,2,6,6-pentamethyl-4-piperidyl) 2-(3,5-di-t-butyl-4-hydroxybenzyl)-2-n-butylmalonate, 1-[2-{3-(3,5-di-t-butyl-4-hydroxyphenyl)propionyloxy}ethyl]-4-[3-(3,5-di-t-butyl-4-hydroxyphenyl)propionyloxy]-2,2,6,6-tetramethylpiperidine, and dimethyl succinate-1-(2-hydroxyethyl)-4-hydroxy-2,2,6,6-tetramethylpiperidine polycondensate.

Further, the tint of the present composition can be improved by the addition of an antioxidant of the phosphite type. Examples of such antioxidants include distearylpentaerythritol diphosphite, tris(2,4-di-t-butylphenyl) phosphite, tris(2-t-butyl-4-methylphenyl) phosphite, bis(2,4-di-t-butylphenyl)pentaerythritol diphosphite, and tetrakis(2,4-di-t-butylphenyl)-4,4'-biphenylene diphosphite.

The synthetic resins to be stabilized according to this invention are polyolefin resins, ABS resin, polystyrene resin, high-impact polystyrene resin, polyamide resin, polyester resin, polycarbonate resin, and polyacetal resin. Of these resins, a polyolefin resin is more effectively stabilized. Such polyolefin resins include poly-$\alpha$-olefins such as low-density polyethylene, medium- to high-density polyethylenes, linear low-density polyethylene, polypropylene and polybutene-1; $\alpha$-olefin copolymers such as random or block copolymers of propylene and ethylene, and ethylene-butene-1 random copolymers; copolymers of $\alpha$-olefins and vinyl monomers such as maleic anhydride-modified polypropylene. Of these polyolefins, polypropylene is most effectively stabilized.

The invention is illustrated below in detail with reference to Reference Examples and Examples, but the invention is not limited thereto.

REFERENCE EXAMPLE 1

Preparation of a Starting Material

Into a 300-ml four-necked flask, were charged 27.8 g of 6-methyl-2,4-di-t-butyl-3-hydroxyphenylacetic acid, 150 ml of toluene and 3 ml of concentrated sulfuric acid. The mixture was heated under reflux for about 5 hours under a nitrogen stream. After completion of the reaction, the reaction mixture was neutralized with an aqueous sodium carbonate solution, washed with water, then dehydrated and freed from the solvent under reduced pressure to obtain 21.5 g (97% yield) of pale yellow 2-methyl-4-t-butyl-5-hydroxyphenylacetic acid which was recrystallized from a chloroform-hexane mixture to yield white crystals melting at 132° to 134° C.

Similar results to above were obtained when p-toluenesulfonic acid, anhydrous aluminum chloride, or boron trifluoride was used in place of the concentrated sulfuric acid.

Elementary analysis:

| | C % | H % |
|---|---|---|
| Calculated for $C_{13}H_{18}O_3$ | 70.2 | 8.2 |
| Found | 70.0 | 8.1 |

$^1$H-NMR (CDCl$_3$) $\delta$[ppm]: 1.33 (s, 9H): 2.20 (s, 3H): 3.50 (s, 2H). 6.50 (s, 1H): 7.01 (s, 1H): 7.40 (s, 1H).

REFERENCE EXAMPLE 2

Preparation of a Starting Material

Into a 1-liter four-necked flask, were charged 58.4 g of methyl 6-methyl-2,4-di-t-butyl-3-hydroxyphenylacetate, 400 ml of toluene, and 6 ml of concentrated sulfuric acid. The mixture was heated under reflux for about 5 hours under a nitrogen stream. After completion of the reaction, the reaction mixture was neutralized with an aqueous sodium carbonate solution, washed with water, dehydrated, and freed from the solvent under reduced pressure to obtain 46.2 g (98% yield) of pale yellow methyl 2-methyl-4-t-butyl-5-hydroxyphenylacetate which was distilled under reduced pressure (1 mmHg, 130°–140° C.) or recrystallized from n-hexane to yield white crystals having a melting point of 100.0°–101.5° C.

Elementary analysis:

|  | C % | H % |
| --- | --- | --- |
| Calculated for $C_{14}H_{20}O_3$ | 71.2 | 8.5 |
| Found | 71.1 | 8.6 |

$^1$H-NMR (CDCl$_3$) δ[ppm]: 1.38 (s, 9H): 2.23 (s, 3H): 3.53 (s, 2H). 3.69 (s, 3H): 5.10 (s, 1H): 6.54 (s, 1H). 7.00 (s, 1H).

EXAMPLE 1

Into a 300-ml four-necked flask, were charged 22.2 g of 2-methyl-4-t-butyl-5-hydroxyphenylacetic acid, 150 ml of toluene, 27.0 g of octadecyl alcohol and 1 g of p-toluenesulfonic acid. The mixture was heated under reflux for about one hour while removing the liberated water from the reaction system. After completion of the reaction, the reaction mixture was freed from the catalyst by washing with water and from the solvent by distillation under reduced pressure to obtain 45.0 g (95% yield) of pale yellow octadecyl 2-methyl-4-t-butyl-5-hydroxyphenylacetate which was recrystallized from methanol to yield white crystals melting at 53.0°–54.5° C.

Elementary analysis:

|  | C % | H % |
| --- | --- | --- |
| Calculated for $C_{31}H_{54}O_3$ | 78.3 | 11.5 |
| Found | 78.0 | 11.6 |

$^1$H-NMR (CDCl$_3$) δ[ppm]: 0.88 (t, 3H): 1.26 (s, 32H): 1.38 (s, 9H). 2.22 (s, 3H): 3.52 (s, 2H): 4.09 (t, 2H). 5.34 (s, 1H): 6.54 (s, 1H): 7.00 (s, 1H).

EXAMPLE 2

Into a 3-l four-necked flask, were charged 76.6 g of 4-t-butyl-5-hydroxy-2-methylphenylacetic acid, 30.0 g of 1,3,5-tris(2-hydroxyethyl)-s-triazine-2,4,6-(1H, 3H, 5H)-trione, 900 ml of toluene and 3.0 g of p-toluenesulfonic acid. The mixture was allowed to refux for about 10 hours by heating under nitrogen stream. After completion of the reaction, the reaction mixture was neutralized with a sodium carbonate aqueous solution, washed with water, dried over anhydrons sodium carbonate and then freed from the solvent under reduced pressure to obtain 93 g (93% yield) of pale yellow 1,3,5-tris{2-(4-t-butyl-5-hydroxy-2-methylphenyl)acetyloxyethyl}isocyanurate, which was recrystallized from n-heptane to yield white crystals melting at 84°–86° C.

Elementary analysis:

|  | C % | H % | N % |
| --- | --- | --- | --- |
| Calculated for $C_{48}H_{63}N_3O_{12}$ | 66.0 | 7.3 | 4.8 |
| Found | 66.3 | 7.5 | 4.7 |

$^1$H-NMR (CDCl$_3$) δ[ppm]: 1.62 (9H, s): 2.16 (3H, s): 3.48 (2H, s). 4.24 (4H, m): 5.86 (1H, s): 6.49 (1H, s). 6.97 (1H, s).

EXAMPLE 3

Into a 500-ml four-necked flask, were charged 128.6 g of methyl 4-t-butyl-5-hydroxy-2-methylphenylacetate and 16.5 g of pentaerythritol. After replacing the air in the flask with dry nitrogen, 0.5 g of sodium methoxide was added to the flask. The mixture was allowed to react at 130° C. for 2 hours, then at 140° to 150° C. under a reduced pressure of about 20 mmHg for 10 hours. During the course of this reaction, along with the progress of reaction 1.5 g of sodium methoxide was added in 3 equal portions. After completion of the reaction, the reaction mixture was cooled to 80° C., neutralized with glacial acetic acid, admixed with toluene, washed with water, dried over anhydrous sodium sulfate, and freed from the solvent under reduced pressure to obtain 101.4 g (88% yield) of pale yellow viscous tetrakis[2-(4-t-butyl-5-hydroxy-2-methylphenyl)acetyloxymethyl]methane which was recrystallized from n-heptane to yield white crystals melting at 89°–91° C.

Elementary analysis:

|  | C % | H % |
| --- | --- | --- |
| Calculated for $C_{57}H_{76}O_{12}$ | 71.8 | 8.0 |
| Found | 71.7 | 8.2 |

$^1$H-NMR (CDCl$_3$) δ[ppm]: 1.33 (36H, s): 2.80 (12H, s): 3.45 (8H, s). 3.79 (8H, s): 5.47 (4H, s): 6.25 (4H, s). 6.99 (4H, s).

EXAMPLE 4

Into a 200-ml four-necked flask, were charged 23.6 g of methyl (2-methyl-4-t-butyl-5-hydroxyphenyl)acetate, 13.0 g of octylalcohol and 0.5 g of sodium methoxide. The mixture was allowed to react at 120° C. for 2 hours, and then at 140° to 150° C. under a reduced pressure of 20 mmHg for 5 hours. During the course of this reaction, along with the progress of reaction 1.5 g of sodium methoxide was added in three equal portions. After completion of the reaction, the reaction mixture was cooled to 80° C., neutralized with glacial acetic acid, then dissolved in toluene, washed with water, dried over anhydrons sodium sulfate, and freed from the solvent under reduced pressure to obtain 29.4 g (88% yield) of viscous octyl 2-methyl-4-t-butyl-5-hydroxyphenylacetate.

Elementary analysis:

|  | C % | H % |
| --- | --- | --- |
| Calculated for $C_{21}H_{34}O_3$ | 75.4 | 10.2 |
| Found | 75.3 | 10.3 |

$^1$H-NMR (CDCl$_3$) δ[ppm]: 0.87 (t, 3H): 1.23 (s, 12H): 1.32 (s, 9H). 2.18 (s, 3H): 3.47 (s, 2H): 4.05 (t, 2H). 5.56 (s, 1H): 6.54 (s, 1H): 6.98 (s, 1H).

EXAMPLE 5

Into a 200-ml four-necked flask, were charged 22.2 g of 2-methyl-4-t-butyl-5-hydroxyphenylacetic acid, 100 ml of toluene and 1 ml of concentrated sulfuric acid, and isobutene was blown into the mixture at 50° to 60° C. for a period of 3 hours. After completion of the reaction, the reaction mixture was freed from the catalyst (sulfuric acid) by washing with water and freed from the solvent under reduced pressure to obtain 26.7 g (96% yield) of yellow t-butyl 2-methyl-4-t-butyl-5-hydroxyphenylacetate, which was recrystallized from n-hexane to obtain white crystals melting at 105.0° to 106.0° C.

Elementary analysis:

|  | C % | H % |
|---|---|---|
| Calculated for $C_{17}H_{26}O_3$ | 73.3 | 9.4 |
| Found | 73.0 | 9.3 |

$^1$H-NMR (CDCl$_3$) δ[ppm]: 1.33 (s, 9H): 1.41 (s, 9H): 2.19 (s, 3H). 3.41 (s, 2H): 5.18 (s, 1H): 6.52 (s, 1H). 6.99 (s, 1H).

EXAMPLE 6

Into a 500-ml four-necked flask, were charged 24.1 g of 2-methyl-4-t-butyl-5-hydroxyphenylacetyl chloride, 300 ml of toluene and 50 ml of pyridine. After replacing air in the reactor by nitrogen, 18.7 g of dodecyl alcohol was added to the mixture at 30° to 40° C., and then the reaction was continued at 30° to 40° C. for about 8 hours. After completion of the reaction, pyridine was neutralized with diluted hydrochloric acid, and the reaction mixture was washed with water, dried over anhydrons sodium sulfate and then freed from the solvent under reduced pressure to obtain 33.2 g (85% yield) of viscous dodecyl 2-methyl-4-t-butyl-5-hydroxyphenylacetate.

Elementary analysis:

|  | C % | H % |
|---|---|---|
| Calculated for $C_{25}H_{42}O_3$ | 76.9 | 10.8 |
| Found | 76.8 | 10.7 |

$^1$H-NMR (CDCl$_3$) δ[ppm] 0.90 (t, 3H): 1.22 (s, 12H): 1.33 (s, 9H). 2.20 (s, 3H): 3.48 (s, 2H): 4.07 (t, 2H). ca. 5.0 (s, 1H): 6.50 (s, 1H): 7.00 (s, 1H).

EXAMPLE 7

A blend of the recipe shown below was thoroughly mixed in a mixer for 5 minutes and then milled in molten state on a mixing roll at 180° C. The resulting compound was molded into a sheet, 1 mm thick, by means of a hot press at 210° C. and test specimens, 40×40×1 mm, were cut out of the sheet. The specimen was heated in a Geer oven at 150° C. and the time, in hours, elapsed before 30% of the specimen area had undergone brittle failure was measured and defined as "enbrittlement induction period" which was used as a criterion for the evaluation of resistances against heat and oxidation. The test results were as shown in Table 2.

Recipe of resin composition:

|  | Parts by weight |
|---|---|
| Unstabilized polypropylene resin | 100 |
| Calcium stearate | 0.1 |
| Test compound | As shown in Table 2 |

The compound numbers I-1, I-4, I-6 and I-7 correspond to those of the present compounds given in Table 1; the compound numbers from AO-1 to AO-6 represent the following compounds:

AO-1: Tris[β-(3,5-di-t-butyl-4-hydroxyphenyl)propionyloxy]ethyl isocyanurate

AO-2: Pentaerythritol tetrakis[β-(3,5-di-t-butyl-4-hydroxyphenyl)propionate]
AO-3: Dilauryl 3,3'-thiodipropionate
AO-4: Distearyl 3,3'-thiodipropionate
AO-5: Pentaerythritol tetrakis(β-hexylthiopropionate)
AO-6: Pentaerythritol tetrakis(β-laurylthiopropionate)

TABLE 2

Stabilizer content (%) and enbrittlement induction period (hour)

| Compound No. | Single stabilizer Run No. | | | | | | | |
|---|---|---|---|---|---|---|---|---|
|  | 1 | 2 | 3 | 4 | 5 | 6 | 7 | 8 |
| Phenol type |  |  |  |  |  |  |  |  |
| I-1 | 0.05 | 0.2 |  |  |  |  |  |  |
| I-7 |  |  | 0.05 | 0.2 |  |  |  |  |
| I-9 |  |  |  |  | 0.05 | 0.2 |  |  |
| I-10 |  |  |  |  |  |  | 0.05 | 0.2 |
| AO-1 |  |  |  |  |  |  |  |  |
| AO-2 |  |  |  |  |  |  |  |  |
| Thioether type |  |  |  |  |  |  |  |  |
| AO-3 |  |  |  |  |  |  |  |  |
| AO-4 |  |  |  |  |  |  |  |  |
| AO-5 |  |  |  |  |  |  |  |  |
| AO-6 |  |  |  |  |  |  |  |  |
| Enbrittlement induction period (hour) | 140 | 310 | 450 | 1320 | 490 | 1480 | 420 | 1380 |

| Compound No. | Combination stabilizer Run No. | | | |
|---|---|---|---|---|
|  | 9 | 10 | 11 | 12 |
| Phenol type |  |  |  |  |
| I-1 | 0.05 | 0.05 |  |  |
| I-7 |  |  | 0.05 | 0.05 |
| I-9 |  |  |  |  |
| I-10 |  |  |  |  |
| AO-1 |  |  |  |  |
| AO-2 |  |  |  |  |
| Thioether type |  |  |  |  |
| AO-3 | 0.2 |  |  |  |
| AO-4 |  |  | 0.2 |  |
| AO-5 |  | 0.2 |  |  |
| AO-6 |  |  |  | 0.2 |
| Enbrittlement induction period (hour) | 530 | 710 | 1540 | 3680 |

| Compound No. | Combination stabilizer Run No. | | | | | |
|---|---|---|---|---|---|---|
|  | 13 | 14 | 15 | 16 | 17 | 18 |
| Phenol type |  |  |  |  |  |  |
| I-1 |  |  |  |  |  |  |
| I-7 |  |  |  |  |  |  |
| I-9 | 0.05 | 0.05 |  |  |  |  |
| I-10 |  |  | 0.05 | 0.05 | 0.05 | 0.1 |
| AO-1 |  |  |  |  |  |  |
| AO-2 |  |  |  |  |  |  |
| Thioether type |  |  |  |  |  |  |
| AO-3 | 0.2 |  |  |  |  |  |
| AO-4 |  |  | 0.2 |  |  |  |
| AO-5 |  | 0.2 |  |  |  |  |
| AO-6 |  |  |  | 0.2 | 0.3 | 0.3 |
| Enbrittlement induction period (hour) | 1260 | 3820 | 1570 | 4400 | 5080 | 5430 |

| Compound No. | Comparative example Run No. | | | | | | | | |
|---|---|---|---|---|---|---|---|---|---|
|  | 19 | 20 | 21 | 22 | 23 | 24 | 25 | 26 | 27 |
| Phenol type |  |  |  |  |  |  |  |  |  |
| I-1 | — |  |  |  |  |  |  |  |  |
| I-7 | — |  |  |  |  |  |  |  |  |
| I-9 | — |  |  |  |  |  |  |  |  |
| I-10 | — |  |  |  |  |  |  |  |  |

TABLE 2-continued

| | Stabilizer content (%) and enbrittlement induction period (hour) | | | | | | | | |
|---|---|---|---|---|---|---|---|---|---|
| AO-1 | | | | | 0.05 | 0.05 | | | — |
| AO-2 | | | | | | | 0.05 | 0.05 | — |
| Thioether type | | | | | | | | | |
| AO-3 | 0.2 | | | | | 0.2 | | | — |
| AO-4 | | 0.2 | | | 0.2 | | | | — |
| AO-5 | | | 0.2 | | | | | 0.2 | — |
| AO-6 | | | | 0.2 | | 0.2 | | | — |
| Enbrittlement induction period (hour) | 100 | 110 | 60 | 50 | 740 | 620 | 820 | 710 | ≦20 |

EXAMPLE 8

In an mixing and grinding machine, 100 parts by weight of powdered ABS resin was dispersed in a suitable amount of methanol. After the addition of a stabilizer under test in an amount shown in Table 3, the mixture was milled to remove the methanol by evaporation. The resulting ABS powder composition was used for the testing. The resistance to heat and oxygen was evaluated by the degree of discoloration after the sample had been aged in a Geer oven at 180° C. The results obtained were as shown in Table 3.

In Table 3, compound Nos. I-1, I-4, I-6, I-7, and AO-1 to AO-6 are the same as those in Table 2.

TABLE 3

| | Stabilizer content (%) and degree of discoloration | | | | | | | | | | | |
|---|---|---|---|---|---|---|---|---|---|---|---|---|
| | Single stabilizer | | | | Combination stabilizer | | | | | | | |
| | 1 | 2 | 3 | 4 | 5 | 6 | 7 | 8 | 9 | 10 | 11 | 12 |
| Phenol type | | | | | | | | | | | | |
| I-1 | 0.3 | | | | 0.3 | 0.3 | | | | | | |
| I-7 | | 0.3 | | | | | 0.3 | 0.3 | | | | |
| I-9 | | | 0.3 | | | | | | 0.3 | 0.3 | | |
| I-10 | | | | 0.3 | | | | | | | 0.3 | 0.3 |
| AO-1 | | | | | | | | | | | | |
| AO-2 | | | | | | | | | | | | |
| Thioether type | | | | | | | | | | | | |
| AO-3 | | | | | | 0.6 | | | | 0.6 | | |
| AO-4 | | | | | 0.6 | | | 0.6 | | | | |
| AO-5 | | | | | | | 0.6 | | | | | 0.6 |
| AO-6 | | | | | | | | | 0.6 | | 0.6 | |

Discoloration
After 30 min.  Pale yellowish brown (columns 1–12)
After 60 min.  Brown (1–4)   Yellowish brown (5–12)

| | Comparative example | | | | | |
|---|---|---|---|---|---|---|
| | 13 | 14 | 15 | 16 | 17 | 18 |
| Phenol type | | | | | | |
| I-1 | | | | | | |
| I-7 | | | | | | |
| I-9 | | | | | | |
| I-10 | | | | | | |
| AO-1 | | | | | 0.3 | 0.3 |
| AO-2 | | | | | | |
| Thioether type | | | | | | |
| AO-3 | 0.6 | | | | | |
| AO-4 | | 0.6 | | | 0.6 | |
| AO-5 | | | 0.6 | | | |
| AO-6 | | | | 0.6 | | 0.6 |

Discoloration
After 30 min. Yellowish (13–16) ... Brown (19) ... brown (20) ... yellowish (21)
After 60 min. Dark brown (19) ... Brown (20)

TABLE 3-continued

| | Stabilizer content (%) and degree of discoloration | | |
|---|---|---|---|
| After 30 min. | Brown | brown | yellowish |
| After 60 min. | Dark brown | | Brown |

| | Comparative example | | |
|---|---|---|---|
| | 19 | 20 | 21 |
| Phenol type | | | |
| I-1 | | | — |
| I-7 | | | — |
| I-9 | | | — |
| I-10 | | | — |
| AO-1 | | | — |
| AO-2 | 0.3 | 0.3 | — |
| Thioether type | | | |
| AO-3 | | | — |
| AO-4 | 0.6 | | — |
| AO-5 | | | — |
| AO-6 | | 0.6 | — |
| Discoloration | | | |
| After 30 min. | Yellowish brown | Pale yellowish | Brownish black |
| After 60 min. | Dark brown | Brown | Brownish black |

What is claimed is:

1. A compound represented by the general formula (I)

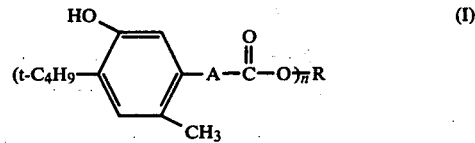

wherein A represents an alkylene group having 1 to 4 carbon atoms and n is an integer of 1, 3 or 4; when n=1, R represents an alkyl group having 1 to 20 carbon atoms; when n=3, R represents a group of the formula

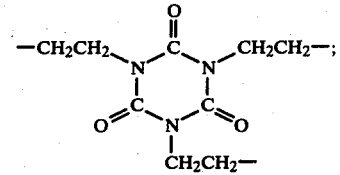

and when n=4, R represents a group of the formula

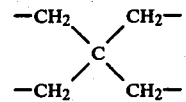

2. A compound represented by the formula

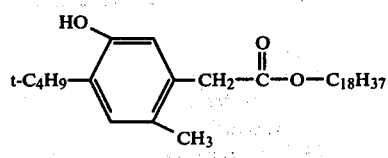

3. A compound represented by the formula

4. A compound represented by the formula

[Structure: 2-hydroxy-3-t-butyl-5-methylphenyl-CH₂CH₂-C(=O)-O-C₁₈H₃₇]

5. A compound represented by the formula

[Structure: 2-hydroxy-3-t-butyl-5-methylphenyl-CH(CH₃)-C(=O)-O-C₁₈H₃₇]

6. A compound represented by the formula

[Isocyanurate ring with three N-CH₂CH₂R substituents, where R = —O—C(=O)—CH₂—(2-hydroxy-3-t-butyl-5-methylphenyl)]

7. A compound represented by the formula

[Isocyanurate ring with three N-CH₂CH₂R substituents, where R = —O—C(=O)—CH₂CH₂—(2-hydroxy-3-t-butyl-5-methylphenyl)]

8. A compound represented by the formula

[Isocyanurate ring with three N-CH₂CH₂R substituents, where R = —O—C(=O)—CH(CH₃)—(2-hydroxy-3-t-butyl-5-methylphenyl)]

9. A compound represented by the formula

[Structure: 2-hydroxy-3-t-butyl-5-methylphenyl-CH₂-C(=O)-O-(CH₂)₃-C]

10. A compound represented by the formula

[Structure: 2-hydroxy-3-t-butyl-5-methylphenyl-CH₂CH₂-C(=O)-O-(CH₂)₃-C]

[Structure: 2-hydroxy-3-t-butyl-5-methylphenyl-CH(CH₃)-C(=O)-O-(CH₂)₃-C]

11. A stabilized synthetic resin composition comprising a synthetic resin and, incorporated therein, a compound represented by the general formula (I)

[Structure (I): 2-hydroxy-3-t-butyl-5-methylphenyl-A-C(=O)-O]$_n$R wherein A represents an alkylene group having 1 to 4 carbon atoms and n is an integer of 1, 3 or 4; when n=1, R represents an alkyl group having 1 to 20 carbon atoms; when n=3, R represents a group of the formula

[Isocyanurate ring with three N-CH₂CH₂— substituents]

and when n=4, R represents a group of the formula

[Neopentyl-like carbon: C with four —CH₂— groups]

12. A synthetic resin composition according to claim 11, wherein the composition contains 0.001 to 5 parts by weight of the compound represented by the general formula (I) for 100 parts by weight of the synthetic resin.

13. A synthetic resin composition according to claim 12, wherein the synthetic resin is a polyolefin.

14. A synthetic resin composition according to claim 13, wherein the polyolefin is polypropylene.

15. A synthetic resin composition according to claim 11, wherein as the compound of general formula (I) use is made of a compound represented by the general formula (II)

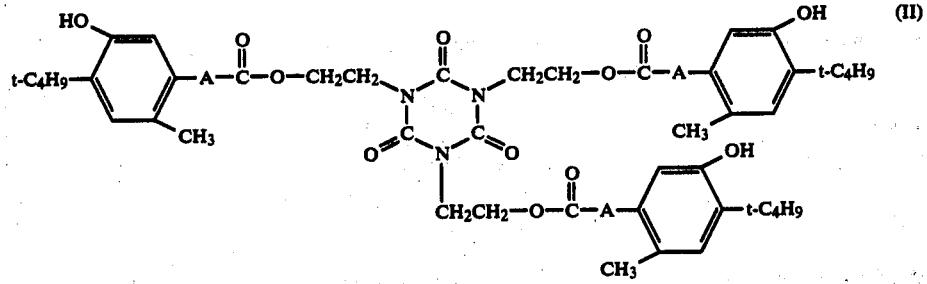

wherein A is as defined above.

16. A synthetic resin composition according to claim 11, wherein as the compound of general formula (I) use is made of a compound represented by the general formula (III)

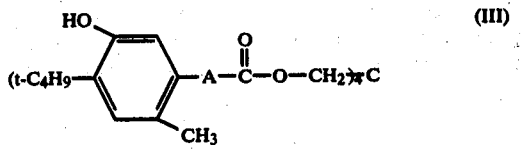

wherein A is as defined above.

17. A stabilized synthetic resin composition comprising a synthetic resin and, incorporated therein, a compound represented by the general formula (I)

wherein A, n and R are as defined above, and a compound represented by the general formula (IV)

```
   CH2CH2COOR                                    (IV)
   |
   S
   |
   CH2CH2COOR
``` wherein R represents an alkyl group having 12 to 20 carbon atoms, in a weight ratio of (I):(IV)=1:1-10.

18. A synthetic resin composition according to claim 17, wherein the total amount of the compound of general formula (I) and the compound of general formula (IV) is 0.001 to 5 parts by weight for 100 parts by weight of the synthetic resin.

19. A synthetic resin composition according to claim 17, wherein the synthetic resin is a polyolefin.

20. A synthetic resin composition according to claim 19, wherein the polyolefin is polypropylene.

21. A synthetic resin composition according to claim 20, wherein as the compound of general formula (I) used is made of a compound represented by the general formula (II)

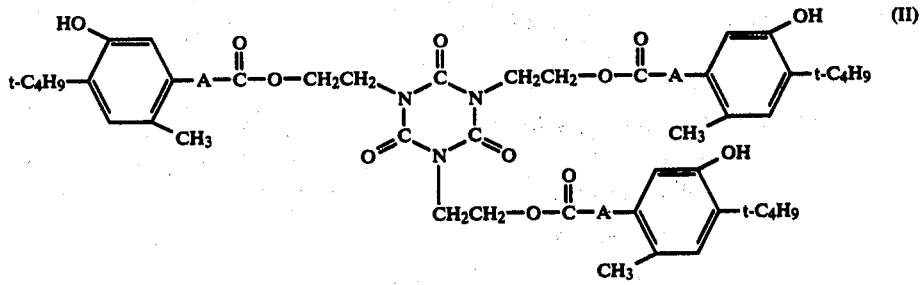

wherein A is as defined above.

22. A synthetic resin composition according to claim 20, wherein as the compound of general formula (I) use is made of a compound represented by the general formula (III)

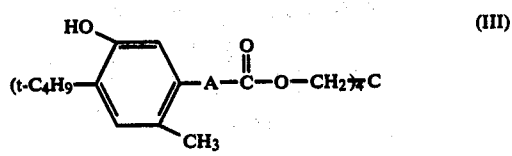

wherein A is as defined above.

23. A synthetic resin composition according to claim 17, wherein the synthetic resin is an ABS resin.

24. A synthetic resin composition according to claim 23, wherein as the compound of general formula (I) used is made of a compound represented by the general formula (II)

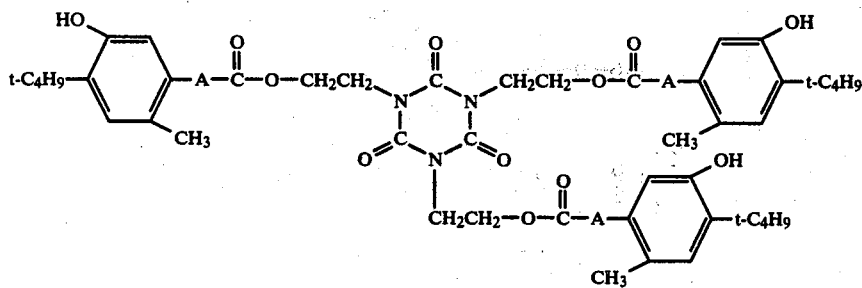

wherein A is as defined above.

25. A synthetic resin composition according to claim 23, wherein as the compound of general formula (I) use is made of a compound represented by the general formula (III)

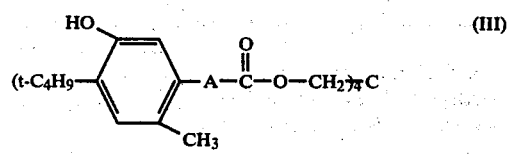

wherein A is as defined above.

26. A stabilized synthetic resin composition comprising a synthetic resin and, incorporated therein, a compound represented by the general formula (I)

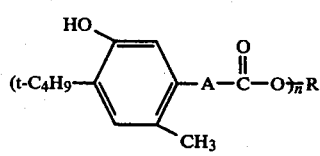

wherein A, n and R are as defined above, and a compound represented by the general formula (V)

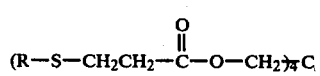

wherein R represents an alkyl group having 4 to 20 carbon atoms, in a weight ratio of (I):(V)=1:1–10.

27. A synthetic resin composition according to claim 26, wherein the total amount of the compound of general formula (I) and the compound of general formula (V) is 0.001 to 5 parts by weight for 100 parts by weight of the synthetic resin.

28. A synthetic resin composition according to claim 26, wherein the synthetic resin is a polyolefin.

29. A synthetic resin composition according to claim 28, wherein the polyolefin is polypropylene.

30. A synthetic resin composition according to claim 29, wherein as the compound of general formula (I) use is made of a compound represented by the general formula (II)

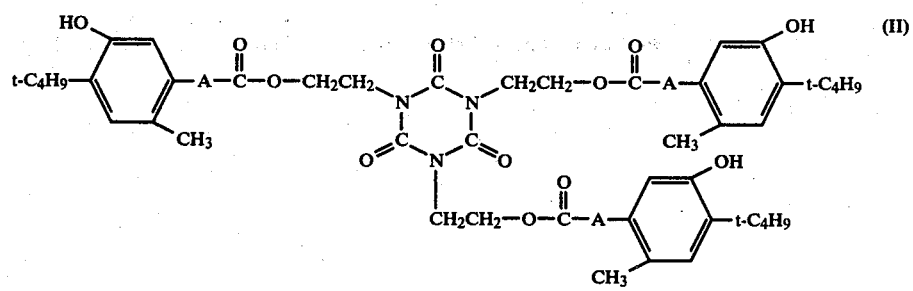

wherein A is as defined above.

31. A synthetic resin composition according to claim 29, wherein as the compound of general formula (I) use is made of a compound represented by the general formula (III)

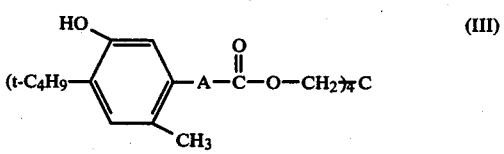

32. A synthetic resin composition according to claim 26, wherein the synthetic resin is a ABS resin.

33. A synthetic resin composition according to claim 32, wherein as the compound of general formula (I) use is made of a compound represented by the general formula (II)

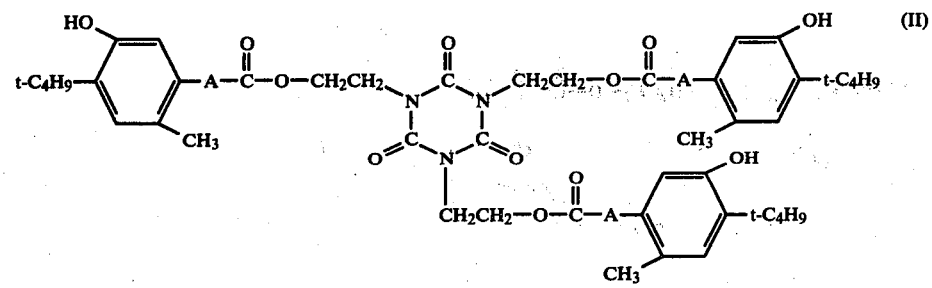 (II)

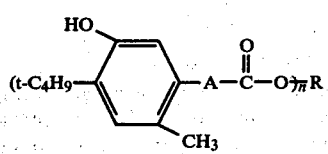 (I)

wherein A is as defined above.

34. A synthetic resin composition according to claim 32, wherein as the compound of general formula (I) use is made of a compound represented by the general formula (III)

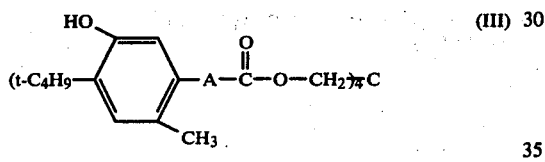 (III)

35. A process for preparing a compound represented by the general formula (I)

wherein A, n and R are as defined above, which comprises reacting an aliphatic alcohol of 1 to 20 carbon atoms, 1,3,5-tris(2-hydroxyethyl)-S-triazine-2,4,6(1H,3H,5H)-trione, or pentaerythritol and a 2-methyl-4-t-butyl-5-hydroxyphenylalkanoic acid represented by the general formula (VI)

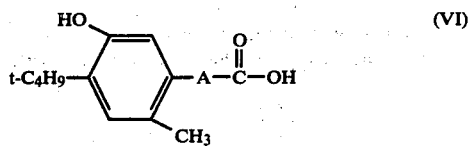 (VI)

wherein A is as defined above, or an acid chloride thereof or a lower alkyl ester thereof.

* * * * *